United States Patent [19]

Shires et al.

[11] 3,969,449

[45] July 13, 1976

[54] VAPORIZING PROCESS

[75] Inventors: Michael John Shires; Stephen Frederick Bush, both of Reading, England

[73] Assignee: Imperial Chemical Industries Limited, London, England

[22] Filed: Mar. 26, 1973

[21] Appl. No.: 344,598

[30] Foreign Application Priority Data

Mar. 29, 1972 United Kingdom ............... 14765/72

[52] U.S. Cl. .............................. 261/153; 260/465.2; 261/156; 261/DIG. 27

[51] Int. Cl.[2] .............................................. B01F 3/04

[58] Field of Search ............ 261/74, 78 A, 151–153, 261/156, 117, 115, DIG. 54, DIG. 27, 76; 260/465.2

[56] References Cited
UNITED STATES PATENTS

| | | | |
|---|---|---|---|
| 1,821,886 | 9/1931 | Fleisher | 261/153 X |
| 1,835,812 | 12/1931 | Ridler | 261/153 |
| 2,289,953 | 7/1942 | Aldridge | 261/153 X |
| 2,514,529 | 7/1950 | Weber | 261/117 |
| 3,142,696 | 7/1964 | Mihara et al. | 260/465.2 |
| 3,153,084 | 10/1964 | Veazey et al. | 260/465.2 |
| 3,460,810 | 8/1969 | Mueller | 261/153 X |
| 3,560,228 | 2/1971 | Engel | 261/78 A X |
| 3,661,973 | 5/1972 | Suzukawa et al. | 260/465.2 |
| 3,836,129 | 9/1974 | Perelmutr et al. | 261/153 X |

*Primary Examiner*—Tim R. Miles
*Assistant Examiner*—Richard L. Chiesa
*Attorney, Agent, or Firm*—Cushman, Darby & Cushman

[57] ABSTRACT

A heat sensitive liquid is vaporized with minimum degradation by introducing it via an atomizer into an enclosed space together with a heated gas under pressure, and so that the gas circulates past heaters which are screened from the atomizer. Useful for vaporizing adipic acid into ammonia gas.

3 Claims, 2 Drawing Figures

U.S. Patent   July 13, 1976   3,969,449

VAPORIZING PROCESS

This invention relates to a process for the vapourisation of a heat-sensitive liquid and to apparatus therefor.

A heat-sensitive liquid to which our invention is particularly applicable is adipic acid which, in the manufacture of adiponitrile, is vapourised into ammonia gas prior to reaction of the mixed vapours in presence of a dehydration catalyst. It has previously been found in such vapourisation of adipic acid that degradation is liable to occur with formation of degradation products such as cyclopentanone as well as tars and coke, with the result that both the yield and the quality of the adiponitrile are lower than desirable, sometimes necessitating special purification stages. Although in the past attempts have been made to overcome this problem, especially by rapid vapourisation, these have not been entirely successful, and in particular it has been found that degradation of adipic acid, and in particular the formation of carbon and tarry residues, is especially liable to occur when the liquid acid comes into intermittent contact with a hot dry surface. In the process of our present invention such contact is substantially reduced or eliminated.

According to the invention we provide a process for the vapourisation of a heat sensitive liquid which comprises introducing into an enclosed space a. the liquid in fine droplet form through an atomising means, and b. a heated gas at a pressure greater than that in the enclosed space so that the gas circulates in the enclosed space past heating means and is further heated, the said heating means being screened from the said atomising means and the liquid droplets being vapourised in the part of the enclosed space screened from the heating means, and removing the vapour from the enclosed space.

Our invention also provides apparatus for the vapourisation of a heat-sensitive liquid comprising an enclosed vessel provided with an inlet for liquid terminating in atomising means therefor, an inlet for heated gas, an exit for vapour, heating means for further heating the gas and screening means screening the atomising means from the heating means and defining a portion of the vessel within which the atomised liquid is vapourised.

A particularly suitable apparatus of our invention comprises a cylindrical vessel having as screening means an open-ended cylindrical inner shell defining an annulus between said shell and the vessel walls. Preferably the walls are heated, for example by external heaters, and the atomising means is within the inner shell.

Figure 1:
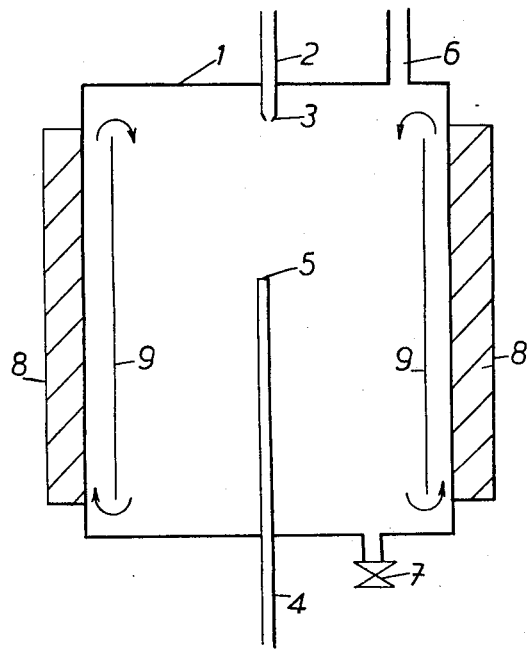
FIG. 1 is a vertical section through a vapourising device embodying the invention.

The process of our invention may be carried out, for example, in the apparatus illustrated in FIG. 1 in which 1 is a vertical cylindrical vessel fitted with an inlet pipe 2 for gas terminating in a jet 3, an inlet pipe 4 for liquid terminating in a hydraulic atomising nozzle 5, an exit pipe 6 for vapour and a blow-down valve 7 for venting any excess liquid from the vessel. The walls of the vessel 1 are fitted with external heaters 8 and a cylindrical shell 9 is fitted inside the vessel forming an annular gap between itself and the walls of the vessel, the shell being spaced from both the top and bottom of the vessel so that the annular gap is accessible from inside the vessel both at the top and the bottom. In operation for the vapourisation of adipic acid into ammonia gas, the ammonia enters the vessel under pressure through the jet 3 while liquid adipic acid is sprayed in through the hydraulic atomising nozzle 5. The pressure under which the ammonia gas enters combined with the geometry of the vaporiser causes the inlet ammonia to circulate and recirculate up the annular gap past the heated walls where it picks up sensible heat so replacing that lost in heating and vapourising the adipic acid. The shell 9 prevents droplets of liquid adipic acid from the nozzle 5 from impinging on the heated walls of the vessel. The mixed vapours of ammonia and adipic acid leave via the exit 6. The recirculation rate and hence the heat transfer are influenced by the particular values of diameter and length of the jet 3, diameter and length of the vessel 1 and diameter of the inner shell 9. For a vessel of given size the recirculation rate is inversely proportional to the jet diameter. We also prefer that the ratio $$\frac{\text{distance from jet 3 to base of vessel 1 }(h)}{\text{inner shell 9 diameter }(d)}$$

should be between 1.5 and 2.

Although it would be possible to provide all of the heat required for the vapourisation of the liquid from the heated gas itself this would require either a large proportion of gas in relation to the proportion of liquid, or a high gas temperature. Such high relative proportions of gas or high temperatures are undesirable in many instances. Thus, in the case of the vapourisation of adipic acid into ammonia gas for conversion of the mixture to adiponitrile, it is preferred to limit the molar ratio of ammonia to adipic acid to from 7 : 1 to 10 : 1, preferably about 8 : 1, and the temperature of the ammonia gas to from 400° to 480°C, preferably about 450°C. In these circumstances about two thirds of the heat required must be introduced through heat applied to the vessel. For convenience of operation the pressure in the vessel may be slightly in excess of atmospheric pressure, e.g. from 0 to 1 atmosphere above atmospheric pressure. Higher pressures than this are possible. Circulation of gas within the vessel depends on the gas entering the vessel being at a higher pressure than that of the vessel. Conveniently the pressure difference is such that the gas leaves the inlet jet at up to sonic velocity and this requires an absolute pressure ratio, inlet jet pressure to vessel pressure, of from 1.6 to 2.4, preferably about 2. The width of the annular gap between the shell and the vessel walls varies depending on the size of the vessel but we prefer that the width of the gap is from 2% to 20% of the diameter of the vessel.

The arrangement described enables a high degree of recycle of gas within the vessel to be achieved, for example between 5 and 50 recycles of gas through the annulus are possible.

When vapourising adipic acid into ammonia gas it is preferred to preheat the adipic acid before feeding it to the atomising nozzle. Adipic acid inlet temperatures are conveniently within the range 150° to 300°C with a preferred range of from 180° to 250°C. The ammonia entering the vessel is also preheated, preferably to a temperature in the range 400° to 480°C. At a mole ratio of ammonia to adipic acid of 8 : 1, the adipic acid vapourises at a temperature of about 275°C. The inner shell 9 of the vessel acts as a secondary heat transfer surface and improves the rate of heat transfer to the gas. It does not reach a sufficiently high temperature to cause excessive degradation of any droplets of adipic acid which fall on it. In operation, temperatures of the inner shell are typically in the range 320° to 390°C. The walls of the vessel are conveniently heated to a temperature in the range 400° to 550°C.

When operated in this way for the vapourisation of adipic acid into ammonia gas there is negligible formation of carbon deposits on the heat transfer surfaces in the vapouriser. Degradation, which was assessed by measuring the proportion of carbon dioxide to adipic acid in the exit gases, is low; it does not normally exceed 2.0% and in the best cases is not more than 0.7%. The carry-over of liquid or solid into the exit gas is very low and normally does not exceed 5 parts per million by weight. Blow down of liquid from the bottom of the vapouriser is usually nil. Overall heat transfer co-efficients are high, being of the order of 20 to 35 CHU/-hour ft²°C.

Figure 2:
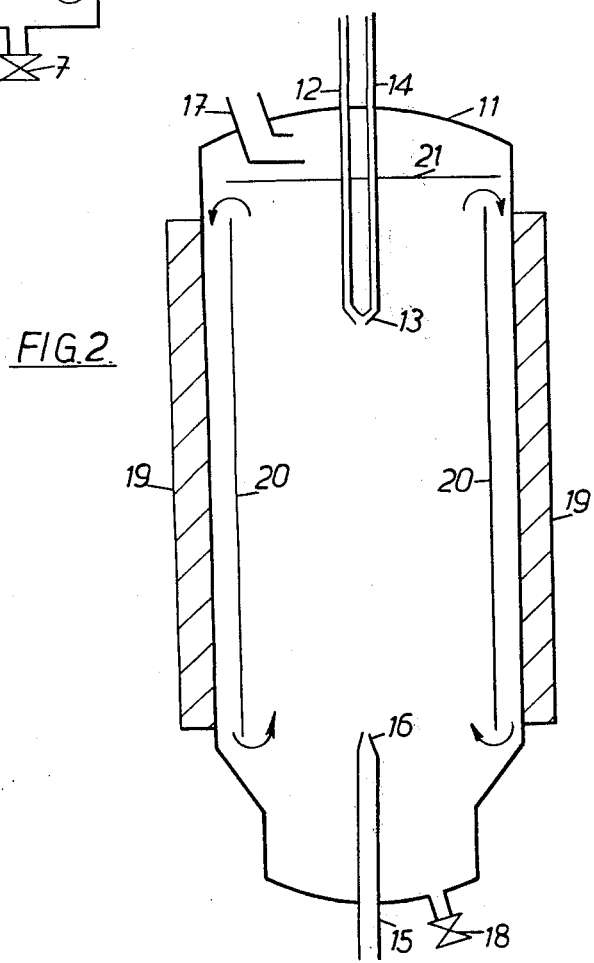
FIG. 2 is a vertical section through a vapourising device illustrating a modification embodying the invention.

The process of our invention may also be carried out, for example, in the apparatus illustrated in FIG. 2 in which 11 is a vertical cylindrical vessel fitted with an inlet pipe 12 for liquid leading to a pneumatic atomising nozzle 13 to which is also connected an inlet pipe 14 for the atomising gas, and also fitted with an inlet pipe 15 for gas under pressure terminating in a jet 16, an exit pipe 17 for vapour, and a blow-down valve 18 for venting any excess liquid from the vessel. The walls of the vessel are fitted with external heaters 19 and a cylindrical shell 20 is fitted inside the vessel forming an annular gap between itself and the walls of the vessel, the shell being spaced from both the top and bottom of the vessel so that the annular gap is accessible from inside the vessel both at the top and the bottom. A baffle plate 21 is also fitted to act as an impingment plate for the ammonia jet.

In operation for the vapourisation of adipic acid into ammonia gas, the ammonia gas enters the vessel under pressure through the jet 16 while liquid adipic acid enters the vessel through the pneumatic atomising nozzle 13 together with the atomising gas which is also ammonia, although other atomising gases, for example nitrogen, may be used. The pressure under which the primary stream of ammonia gas 15, 16 enters combined with the geometry of the vaporiser causes the inlet ammonia stream from the jet 16 to circulate and recirculate down the annular gap past the heated walls where it picks up sensible heat. The shell 20 prevents droplets of liquid adipic acid from impinging on the heated walls of the vessel. The mixed vapours of ammonia and adipic acid leave via the exit 17.

Conditions under which vapourisation occurs in this second apparatus are very similar to those already described for the first apparatus. Typical operating conditions are as follows:

| | |
|---|---|
| Ammonia inlet pressure | 25 – 50 p.s.i.g. |
| Vessel pressure | 5 – 25 p.s.i.g. |
| Ammonia inlet temperature | 450°C – 480°C |
| Adipic acid inlet " | 180°C |
| Exit gas " | 330°C |
| Heated walls at | 450 – 550 20 C. |

The proportion of ammonia gas required for atomising the adipic acid in the pneumatic atomising nozzle is about 3% by weight of the adipic acid to be atomised. In an apparatus of this kind of appropriate size it is possible to vapourise adipic acid at a rate of 3500 lbs./hr. into ammonia supplied at a rate of 3500 lbs./hr., 200 lbs./hr. of which is used for atomising the adipic acid.

The apparatus illustrated in FIG. 2, however, is not quite as thermally efficient as that shown in FIG. 1 because the circulatory flow is opposite to that which would be due to natural convection. That of FIG. 1 also has the advantage that the exit gases are drawn from the hottest part of the vessel.

It is an advantage of the process of our invention that heat-sensitive liquids can be vapourised with a minimum of degradation and without the formation of coke or involatile tars on the heat transfer surfaces which often occurs when heat-sensitive organic liquids impinge intermittently on hot dry surfaces. The process can be operated with substantially no blowdown from the vapouriser. These advantages are particularly marked at gas exit temperatures of 350°C and above. The apparatus used in our process is simple and has no moving parts. Although the method is of special applicability to the vapourisation of adipic acid into ammonia gas it is also applicable to the vapourisation of other heat sensitive liquids, for example tolylene di-= isocyanate, and also, for example, in the process of spray drying.

The invention is illustrated but not limited by the following Examples in which the parts and percentages are by weight.

EXAMPLES 1 to 8

An apparatus as illustrated in FIG. 1 and described hereinbefore was used for the vapourisation of adipic acid into ammonia gas. The apparatus used had a diameter of 12 inches and a height of 18 inches. The width of the annular gap was varied. Results achieved are given in the following table.

| EXAMPLE NO. | 1 | 2 | 3 | 4 | 5 | 6 | 7 | 8 |
|---|---|---|---|---|---|---|---|---|
| Width of annular gap (inches) | 1 | 0.5 | 0.5 | 0.5 | 0.5 | 2 | 0.5 | 0.5 |
| Adipic acid feed rate (lbs./hr.) | 20.0 | 19.0 | 20.5 | 20.0 | 20.0 | 20.0 | 23.8 | 24.2 |
| Ammonia feed rate (lbs./hr.) | 19.0 | 18.5 | 19.3 | 24.4 | 14.1 | 19.6 | 24.4 | 25.1 |
| Adipic acid inlet temp. (°C) | 191 | 248 | 188 | 190 | 188 | 191 | 190 | 192 |
| Ammonia inlet temp. (°C) | 431 | 443 | 443 | 440 | 442 | 430 | 402 | 411 |
| Gas exit temp. (°C) | 374 | 375 | 368 | 377 | 393 | 377 | 358 | 359 |
| Ammonia inlet pressure (psig) | 21 | 22 | 21 | 30 | 16 | 24 | 26 | 34 |
| Gas exit pressure (psig) | 7 | 9 | 7 | 10 | 5 | 8 | 14 | 12 |
| Degradation (%) | 1.5 | — | 0.8 | 0.7 | 2.2 | 1.0 | 0.8 | 0.9 |
| Overall heat transfer co-efficient | 28.7 | 28.0 | 25.6 | 33.0 | 32.8 | 30.2 | 26.1 | 24.5 |
| Recycle ratio up annulus | — | 37 | 33 | 24 | 27 | 22 | 30 | 28 |

EXAMPLES 9 to 10

An apparatus as illustrated in FIG. 2 and described hereinbefore was used for the vapourisation of adipic acid into ammonia gas. The apparatus used had a diameter of 4 ft. 3 inches and a height of 10 ft. The width of the annular gap was 3 inches. Results achieved are given in the following Table.

| EXAMPLE NO. | 9 | 10 |
|---|---|---|
| Adipic acid feed rate (lbs./hr.) | 4000 | 3200 |
| Ammonia feed rate (lbs./hr.) | 4000 | 3400 |
| Adipic acid inlet temp. (°C) | 187 | 188 |
| Ammonia inlet temp. (°C) | 465 | 480 |
| Gas exit temp. (°C) | 320 | 330 |
| Ammonia inlet pressure (psig) | 26 | 21 |
| Gas exit pressure (psig) | 7 | 10 |
| Degradation (%) | 2.2 | 1.2 |
| Overall heat transfer co-efficient | 22.2 | 19.9 |

We claim:

1. A process for the vapourisation of a heat-sensitive liquid which comprises introducing into an enclosed space
   a. the liquid in fine droplet form through an atomising means, and
   b. a heated gas at a pressure greater than that in the enclosed space so that the gas circulates and recirculates in the enclosed space past heating means and is further heated, screening the said heating means from the said atomising means and vapourizing the liquid droplets in the part of the enclosed space screened from the heating means by the heated inlet gas and the further heated recirculating gas and removing the vapour from the enclosed space.

2. The process of claim 1 including introducing the heated gas into the enclosed space through a jet so that the absolute pressure ratio, gas inlet jet pressure to vessel pressure, is from 1.6 to 2.4.

3. The process of claim 1 including circulating the gas first through an open-ended cylindrical inner shell providing the screening means in a cylindrical vessel, the walls of which are heated, and secondly through the annulus defined between the shell and the vessel walls, and repeating these steps cyclically until the degree of recycle of gas through the annulus is from 5 to 50 recycles.

* * * * *